March 22, 1955 F. MEILLAND Plant Pat. 1,367
ROSE PLANT
Filed July 6, 1954
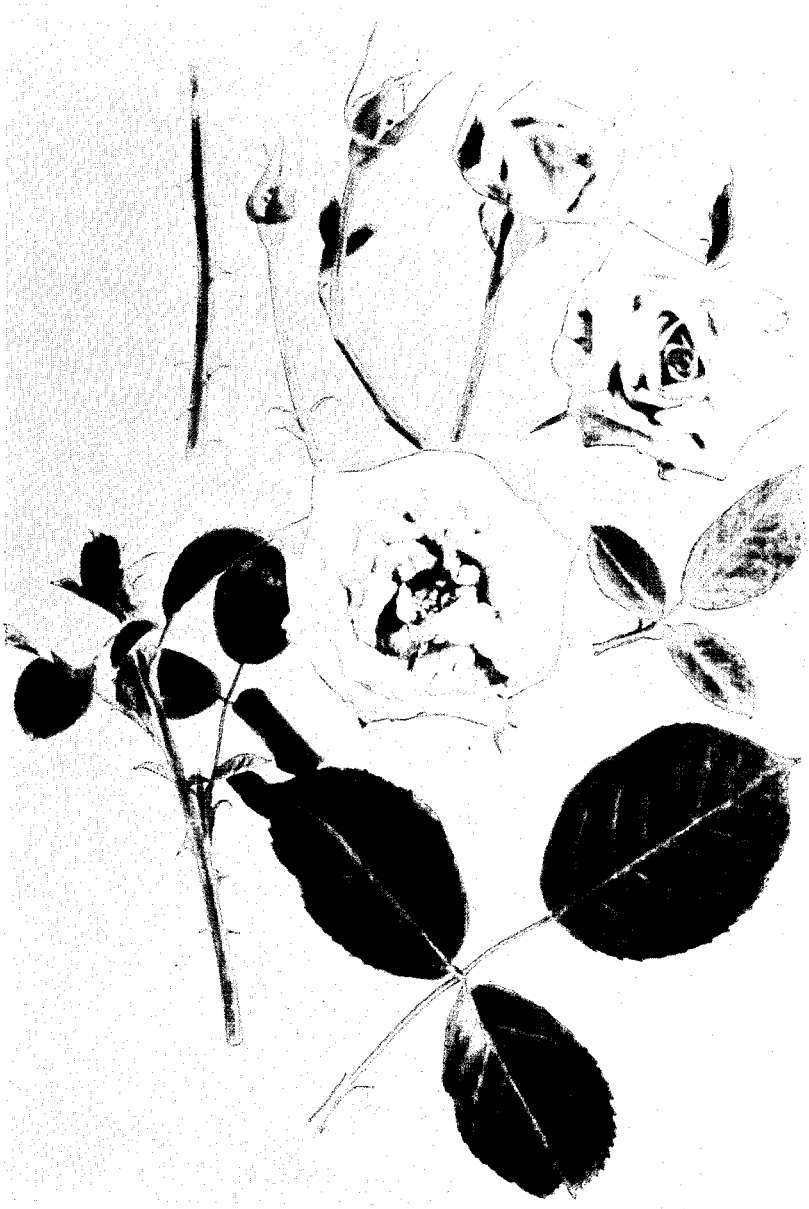
Inventor.
Francis Meilland
By: Robb & Robb
Attorneys United States Patent Office Plant Pat. 1,367

Patented Mar. 22, 1955

1,367

ROSE PLANT

Francis Meilland, Cap Azura, Cap d'Antibes, France, assignor to The Conard-Pyle Company, West Grove, Pa., a corporation of Pennsylvania Application July 6, 1954, Serial No. 441,698

Claims priority, application France July 7, 1953

1 Claim. (Cl. 47—61)

The present invention relates to a new and distinct variety of rose plant of the hybrid tea class, which was originated by me by crossing the variety "Happiness," known in France as "Rouge Meilland" (Plant Patent No. 911) with the variety "Independence," known in Germany as "Kordes' Sondermeldung" (Plant Patent No. 1,036).

As the result of this cross, I have produced a new variety of rose plant which is particularly distinguished as to novelty by the following unique combination of characteristics which are not found in either parent or in any other rose variety at present known to me in commerce:

(1) An unusually brilliant Scarlet color tonality of the flowers which are shaded at the center of the newly opened blooms with Currant Red color;

(2) The very double, almost zinnia-like form of the fully open flower, and the unusually firm, rigid and heavy petals which give the flower lasting qualities well above the average as compared with other known varieties;

(3) The bushy, upright and vigorous habits of growth of the plant, and its continuity of bloom; and (4) The superior value of the variety for commercial greenhouse plantings for the cut-flower trade, as an outdoor rose for amateur growers, for garden decoration and for cut-flower uses.

Asexual reproduction of my new variety in France, as well as at West Grove, Pennsylvania, U. S. A., shows that the foregoing characteristics and distinctions come true to form and are established and transmitted through succeeding propagations.

The accompanying drawing shows typical specimens of the flowers and foliage of my new variety as depicted in color as nearly true as it is reasonably possible to make the same in a color illustration of this character.

The following is a detailed description of my new variety, with color terminology in accordance with Robert F. Wilson's Horticultural Colour Chart, except where general color terms of ordinary dictionary significance are obvious:

Type: Hardy; bush; greenhouse and outdoor; seedling; for cut flowers and for garden decoration.

Class: Hybrid tea.

Breeding: Seedling.

*Seed parent.*—"Happiness" ("Rouge Meilland").

*Pollen parent.*—"Independence" ("Kordes' Sondermeldung").

Propagation: Holds its distinguishing characteristics through succeeding propagations by budding.

FLOWER

Locality where grown and observed: West Grove, Pennsylvania, U. S. A.

Flowers borne: Generally singly; on medium length stems of normal strength.

Quantity of bloom: Free to abundant outdoors.

Continuity: Continuous.

Fragrance: None.

Bud:

*Peduncle.*—Medium length; medium caliper; stiff; almost smooth; few Brown prickles. Color—Lettuce Green, Plate 861/3, overlaid with Reddish color on some parts.

*Before calyx breaks.*—Size—medium. Form—medium length; globular; with a conspicuous neck; with foliaceous appendages on the surface of the bud; with slender, little-cut, bristle-like foliaceous parts extending beyond the tip of the bud equal to ½ or more of its length.

*As calyx breaks.*—Color—Cardinal Red, Plate 822, marked with Indian Lake, Plate 826; all becoming Indian Lake, Plate 826 before the petals open.

*As first petal opens.*—Size—medium. Form—globular.

Color: Outside—Currant Red, Plate 821/3 at outer quarter, shading to Cardinal Red, Plate 822/1, and then to Indian Lake, Plate 826/1. Inside—Scarlet, Plate 19 at outer quarter, shading to Geranium Lake, Plate 20 toward base, and touched at base with a small suffusion of Dianthus Purple, Plate 730/1.

*Opening.*—Opens up well.

Bloom:

*Size (when fully open).*—Medium; from 3 inches to 3¼ inches.

*Petalage.*—Very double; from 72 to 82 petals; arranged regularly.

*Form.*—Cupped at first, but becoming very full and flat, with closely overlapping petals; petals being at first loosely rolled outward, but becoming loosely rolled outward, with the outer petals folded to points later at maturity.

Petals: Thick; tough; leathery; with inside velvety and outside satiny.

*Shape.*—Outer petals—obovate, with 1 notch. Intermediate petals—obovate; generally with no notches. Inner petals—round; sometimes with 1 notch, but often none.

This description of a newly opened flower was made from a rose grown outdoors in the month of June, at West Grove, Pennsylvania, U. S. A.:

Color:

*Outer petal.*—Outside surface—Rose Madder, Plate 23 at outer third of petal, shading to Blood Red, Plate 820/2 and tipped with a small suffusion of Dianthus Purple, Plate 730/2 at point of attachment. Inside surface—Geranium Lake, Plate 20 over most of petal, touched with Dianthus Purple, Plate 730/2 at base.

*Intermediate petal.*—Outside surface—from Claret Rose, Plate o21 over the outer half to Cardinal Red, Plate 822/2, suffused at base with Dianthus Purple, Plate 730/3. Inside surface—Scarlet, Plate 19 over all of petal except for zone at base which is Dianthus Purple, Plate 730/1.

*Inner petal.*—Outside surface—Indian Lake, Plate 826 over entire petal to point of attachment which is lightly suffused with Dianthus Purple, Plate 730/1. Inside surface—Currant Red, Plate 821 over entire petal except small zone at base which is Dianthus Purple, Plate 730/1.

This description was made from a rose that was open for three days outdoors in the month of June, at West Grove, Pennsylvania, U. S. A.:

Color:

*Outer petal.*—Outside surface—Solferino Purple, Plate 26 over most of petal; side margins are Rose Madder, Plate 23, tipped with White at point of attachment. Inside surface—Scarlet, Plate 19 over most of petal; suffused at base with Fuchsine Pink, Plate 627.

*Inner petal.*—Outside surface—China Rose, Plate o24 over entire petal except for slight suffusion of Fuchsine Pink, Plate 627/2 at base. Inside surface—Scarlet, Plate 19/1 over entire petal except for small suffusion of Neyron Rose, Plate 623, at base.

General color effect:

*Newly opened flower.*—Currant Red center, surrounded by many scarlet outer petals.

*3-days open.*—Medium scarlet throughout.

Behavior: Drop off cleanly.

Flower longevity:

*On bush in garden.*—6 days in June.

*Cut roses grown outdoors and kept at living-room temperatures.*—5 or 6 days in June.

REPRODUCTIVE ORGANS

Stamens: Medium number; arranged irregularly about pistils.
Filaments: Few; most with anthers; medium length. Color—China Rose, Plate o24/2.
Anthers: All open at once; medium size; occasionally an anther fused with a petaloid. Color—Saffron Yellow, Plate 7/2.
Pollen: Abundant. Color—Lemon Yellow, Plate 4.
Pistils: Many.
Styles: Uneven, medium length; from thin to medium caliper; loosely bunched.
Stigma: Color—yellow.
Ovaries: Some protruding from calyx.
Hips: None.
Sepals: Permanent; from medium length to long; spear-shaped; curled.
Seeds: None.

PLANT

Foliage:
*Leaves.*—Usually compound of 5, but sometimes 3 or 7 leaflets; normal abundance; medium size; leathery.
*Leaflets.*—Shape—Oval, with acute apex. Base—Variable; mostly rounded, but some acute. Margin—Simply serrate.
*Color.*—Mature: Upper surface—Spinach Green, Plate o96/1; under surface—Slightly lighter than Willow Green, Plate ooo862/1. Young: Upper surface—Maroon, Plate 1030; under surface—Garnet Brown, Plate oo918.
*Rachis (the supporting stem of the compound leaf.)*—Medium weight.
Upper side—Grooved; prickly.
Under side—Sparsely thorny.
*Stipules.*—Medium length; medium width; with medium length points turning out at an angle of more than 90°; recurved toward stem.

*Disease resistance.*—Very good resistance to black-spot and average resistance to rust, as compared with other varieties grown under comparable cultural conditions at West Grove, Pennsylvania, U. S. A.
Growth:
*Habit.*—Bushy; upright; much-branched.
*Growth.*—Free to vigorous.
*Canes.*—Medium caliper.
*Main stems.*—Color—Fern Green, Plate o862, sometimes showing reddish coloration on one side.
Thorns—Several; medium length; hooked downward; with medium length, oval, narrow base.
Prickles—Several. Color—red.
Hairs—None.
*Branches.*—Color—Fern Green, Plate o862, sometimes with reddish overlying coloration.
Thorns—Several; medium length; hooked downward; with medium length, narrow, oval base.
Prickles—Several. Color—red.
Hairs—None.
*New shoots.*—Color—Lettuce Green, Plate 861/3, with overlying reddish coloration on one side.
Thorns—Several; medium length; hooked downward; with medium length, narrow, oval base.
Prickles—Few. Color—reddish.
Hairs—None.

I claim:

A new and distinct variety of rose plant of the hybrid tea class, substantially as herein shown and described, characterized particularly as to novelty by the unusually brilliant scarlet and currant red general color tonality of the bloom, the very double form of the bloom, with unusually firm, rigid and heavy petals, with attendant superior lasting qualities, the vigorous, upright and bushy habits of growth of the plant, and by its superiority for both greenhouse and garden plantings.

No references cited.